United States Patent
Bosquet et al.

(10) Patent No.: US 6,438,397 B1
(45) Date of Patent: Aug. 20, 2002

(54) METHOD AND APPARATUS FOR ANALYTE DETECTION USING INTRADERMALLY IMPLANTED SKIN PORT

(76) Inventors: Gerald G. Bosquet, 29 Village Sq., P.O. Box 201, Chelmsford, MA (US) 01824; Gerald L. Cote, 1204 Neal Pickett Dr.; Ashok Gowda, 100 Redmond Dr., both of College Station, TX (US) 77840; Roger McNichols, 3715 Sweetbriar, Bryan, TX (US) 77802; Sohi Rastegar, P.O. Box 2314, College Station, TX (US) 77841

(*) Notice: Subject to any disclaimer, the term of this patent is extended or adjusted under 35 U.S.C. 154(b) by 0 days.

(21) Appl. No.: 09/429,191

(22) Filed: Oct. 28, 1999

(51) Int. Cl.$^7$ ................................................. A61B 5/00
(52) U.S. Cl. ........................ 600/310; 600/344; 600/322
(58) Field of Search .................. 600/309–311, 322–328, 600/339–344, 473, 476, 316; 356/39–42

(56) References Cited

U.S. PATENT DOCUMENTS

| | | | | |
|---|---|---|---|---|
| 5,001,054 A | * | 3/1991 | Waagner | 435/14 |
| 5,024,226 A | * | 6/1991 | Tan | 600/340 |
| 5,079,421 A | * | 1/1992 | Knudson et al. | 250/343 |
| 5,582,184 A | * | 12/1996 | Erickson et al. | 600/576 |
| 5,662,616 A | * | 9/1997 | Bousquet | 604/175 |
| 5,706,807 A | * | 1/1998 | Picha | 600/345 |
| 6,049,727 A | * | 4/2000 | Crothall | 600/310 |
| 6,122,536 A | * | 9/2000 | Sun et al. | 600/341 |

* cited by examiner

Primary Examiner—Eric F. Winakur
Assistant Examiner—Matthew Kremer

(57) ABSTRACT

A transcutaneous, implantable skin port sensor includes an access component and a sensor component, both of which can be made from inexpensive biocompatible materials. The access component provides a biological seal that forms around the skin port sensor. The sensor component facilitates non-invasive optically based measurement of analytes by providing a window to the body which avoids changes in the optical signal due to variations in skin optics, optical pathlength, ambient temperature and probe pressure. Tissue ingrowth or interstitial fluid in a through portion downstream of the optical window serves as the sample for the non-invasive, optically based measurement.

26 Claims, 4 Drawing Sheets

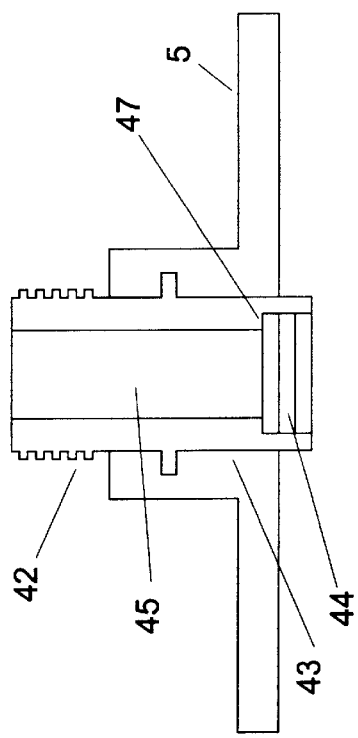
FIGURE 1-B
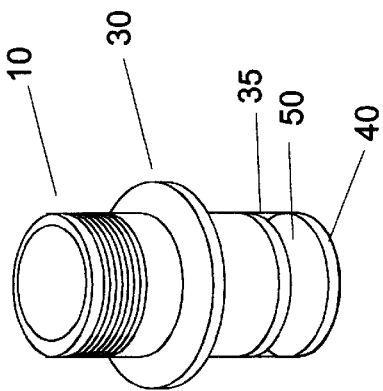
FIGURE 1-D
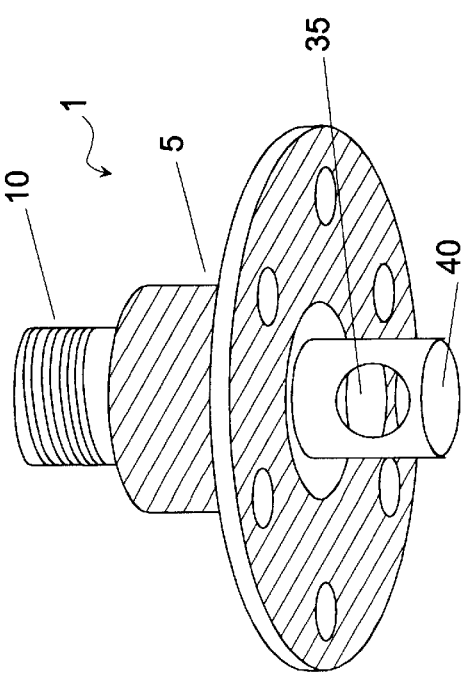
FIGURE 1-A
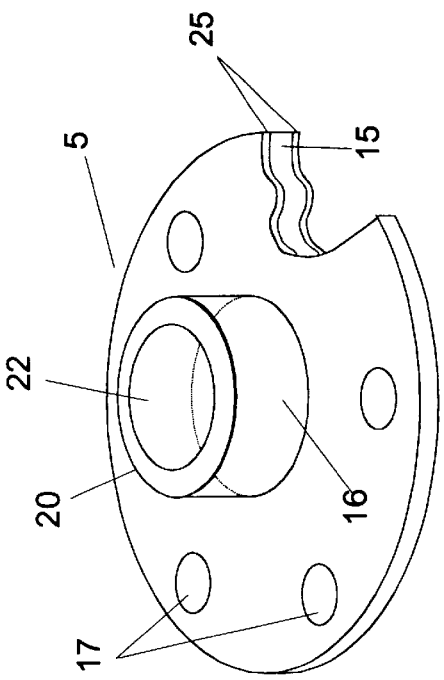
FIGURE 1-C

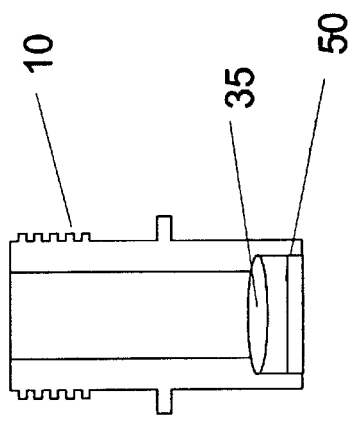
FIGURE 2-C
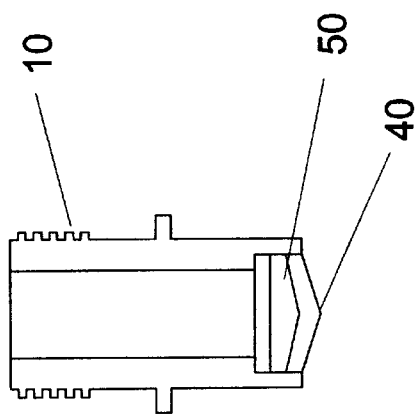
FIGURE 2-B
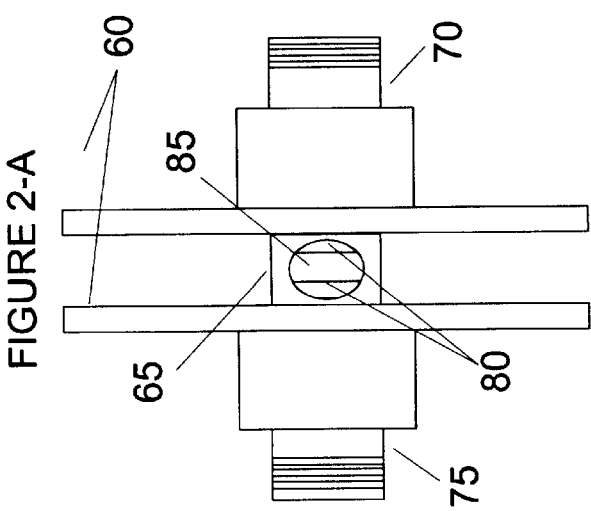
FIGURE 2-A
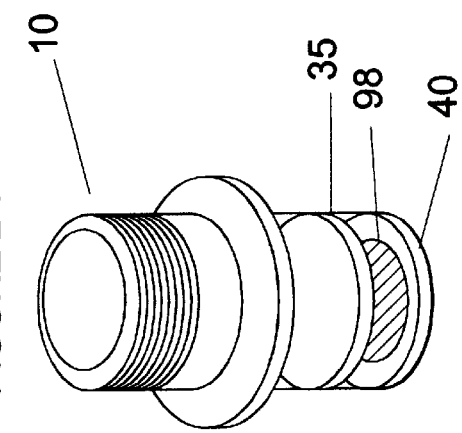
FIGURE 2-F
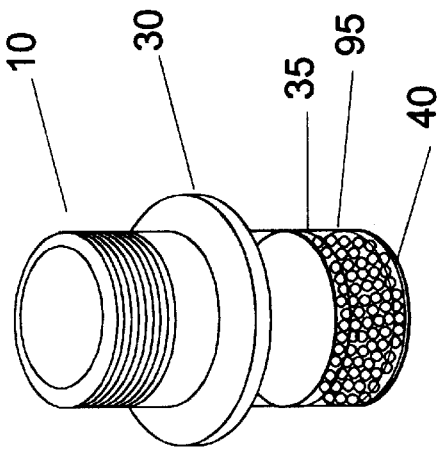
FIGURE 2-E
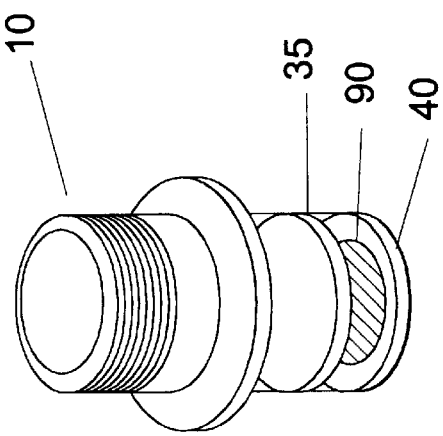
FIGURE 2-D FIGURE 2-G
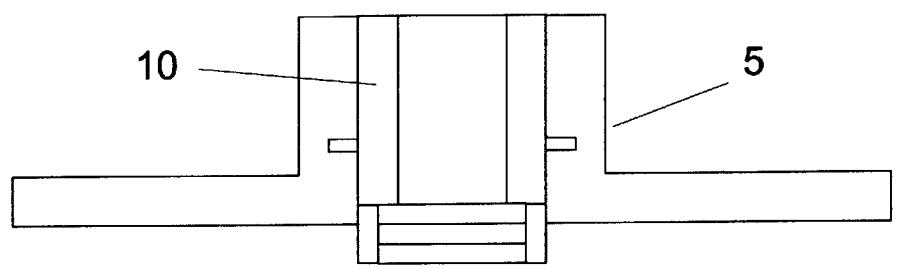
FIGURE 2-H
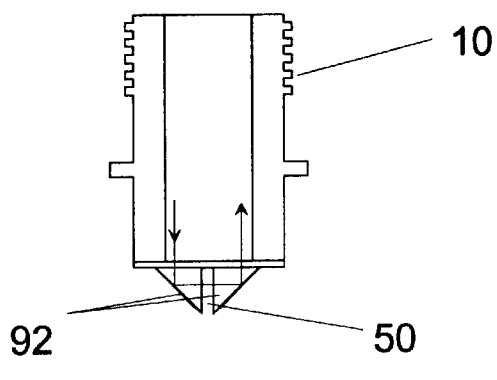
FIGURE 2-I
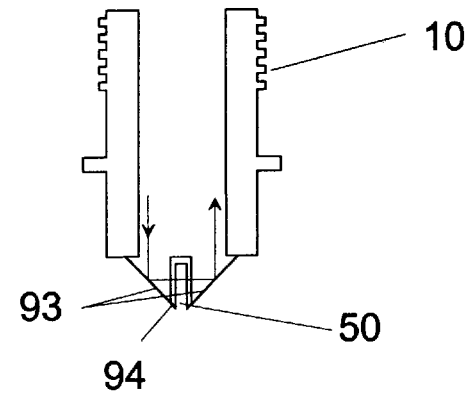

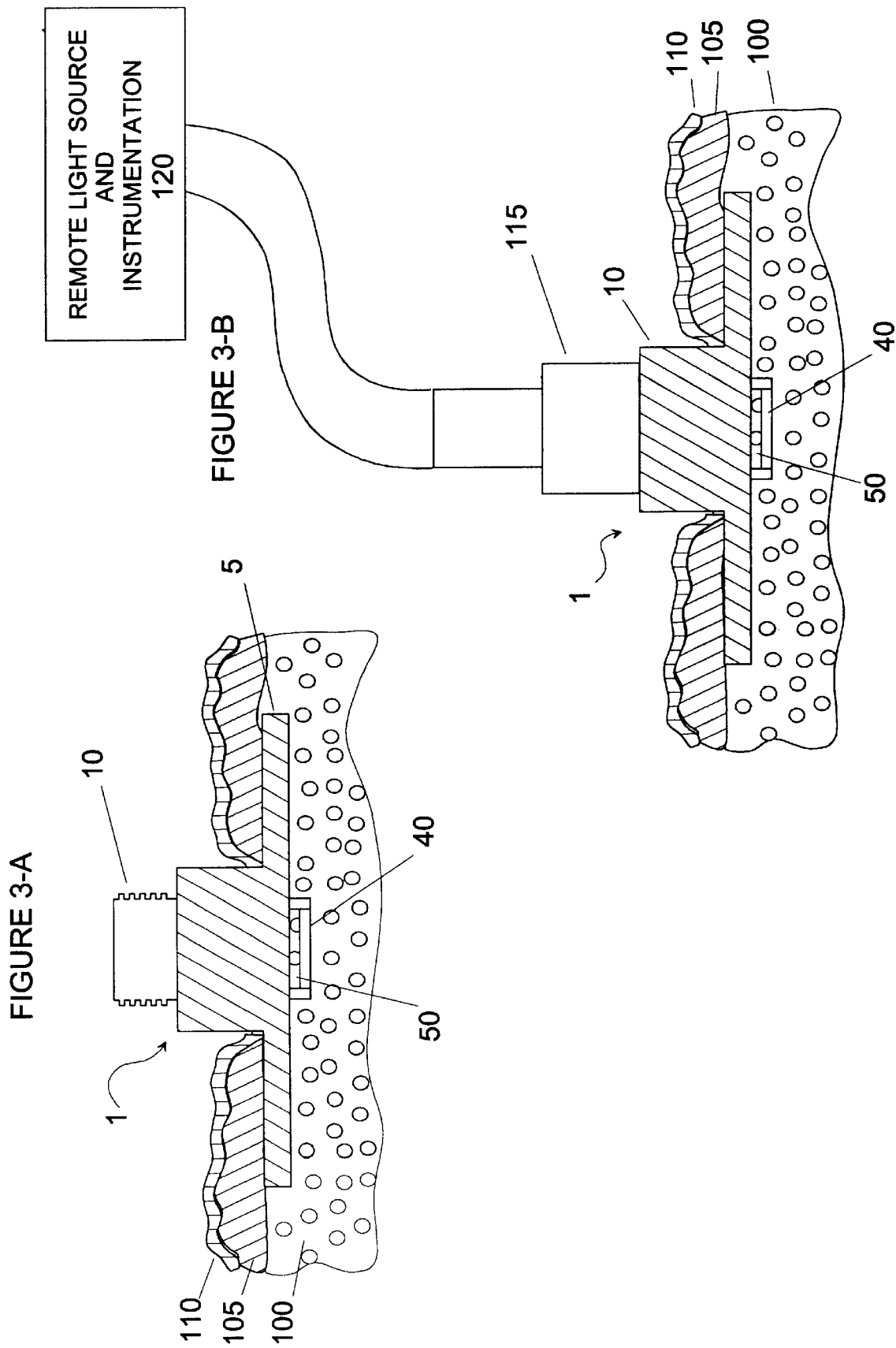

METHOD AND APPARATUS FOR ANALYTE DETECTION USING INTRADERMALLY IMPLANTED SKIN PORT

BACKGROUND OF THE INVENTION

The invention is directed to a method and an apparatus for intradermal implantation of a device to facilitate non-invasive measurement of analytes including, but not limited to, glucose, cholesterol, lactate, bilirubin, blood gases ($pO_2$, $pCO_2$pH), urea, creatinine, phosphate, myoglobin, and hormones.

Diabetes mellitus is a chronic systemic disease characterized by disorders in the metabolism of insulin, carbohydrate, fat, and protein as well as in the structure and function of blood vessels. Currently, diabetes is a leading cause of death in the United States, and more than 16 million Americans are believed to have this disease. Intensive management of blood sugars through frequent monitoring is effective to prevent, or at least slow, the progression of diabetic complications such as kidney failure, heart disease, gangrene, and blindness.

Maintaining blood glucose levels near normal levels can only be achieved with frequent blood glucose monitoring so that appropriate actions can be taken, such as insulin injections, proper diet, or exercise. Unfortunately, the current method of sensing is a colorimetric/electro-enzymatic approach, which is invasive, requiring a finger stick to draw blood each time a reading is needed. This approach is both time-consuming and painful. Therefore, there is a lack of compliance among the diabetic population for even monitoring their levels once per day, which is far below the recommended five or more times daily.

Minimally invasive approaches have been investigated as a less painful method of estimating blood glucose concentrations. These approaches involve disruption of the skin barrier without puncturing a capillary to obtain a small sample of interstitial fluid for subsequent measurement of glucose concentration. Various methods have been used including electrical current, suction, penetration, and ultrasound for obtaining interstitial fluid samples. While measurement of glucose in interstitial fluid is potentially feasible, it has associated limitations. The accuracy of this method has not yet been sufficiently demonstrated for commercial viability. Factors such as edema, thick skin, hypothermia, obesity, which is a common factor in diabetes, or local blood flow changes may affect accuracy. There may still be discomfort associated with obtaining interstitial fluid as the skin barrier must still be penetrated. Finally, contaminants in such small samples would likely cause large variations in measurement accuracy.

A completely non-invasive approach would result in the largest improvement in patient compliance for monitoring blood glucose levels. Non-invasive blood glucose monitoring involves applying a radiation to tissue and measuring the interaction with glucose to determine the concentration. Promising optical-based technologies for noninvasive measurement of glucose concentration include near-infrared (NIR) light spectroscopy, mid-infrared radiation (MIR) spectroscopy, and optical rotation of polarized light. Examples of such non-invasive techniques and associated apparatuses are set forth in U.S. Pat. Nos. 5,703,364, 5,574,283, 5,460,177, 5,379,764, 5,360,004 and 5,077,476.

Although the use of NIR spectroscopy combined with the prudent use of chemometric techniques allow predictive models to be obtained that relate directly to the chemical spectroscopic signature, there are drawbacks to such approaches. There is the lack of repeatability of NIR measurements in vivo both within and between patients. The attendant signal variations are due in part to changes in the skin tissue optics between patients, the lack of a repeatable pathlength inherent in using a diffusely reflected photon approach, and temperature variations at the surface of the body. In addition, the pressure with which a probe is applied to the skin surface can play a major role in the predictive capability of the technique. None of the previous approaches to non-invasive glucose sensing have attempted to address these important issues of skin optics and pathlength that will inevitably have significant variation across the population of diabetics.

SUMMARY OF THE INVENTION

The present invention is therefore directed to a method and an apparatus for analyte detection which substantially overcomes one or more of the problems due to the limitations and disadvantages of the related art.

An object of the present invention is to provide an implant that would facilitate non-invasive optical measurements of analyte concentrations in the tissue, blood or interstitial space.

Another object of the present invention is to provide an infection-free implant that would eliminate problems related to skin optics by providing a window to the body that could be used with a variety of optical approaches such as near-infrared (NIR) absorption spectroscopy or optical rotation of polarized light to determine the concentration of the analyte.

A further object of the present invention is to provide an implant with a fixed optical pathlength minimizing variations inherent in previous approaches.

Yet another object of the present invention is to provide an implant to minimize variations in optical signals due to ambient temperature fluctuations.

An additional object of the present invention is to provide an implant to minimize probe movement during optical measurements.

Another object of the present invention to provide a rigid implant with a fixed optical window to minimize variations in optical signals due to the probe or the device.

Yet another object of the present invention is to provide an implant that demonstrates signal variations due to analytes in the blood thereby providing a direct measurement of the concentration in the blood.

Further objects and advantages are to provide an implant which can be used easily and conveniently by patients in their home, which is simple and inexpensive to manufacture, which can be used across a population of patients, which facilitates better patient compliance for monitoring important analytes in order to maintain normal blood concentration levels, and which obviates the need for acquiring a fluid sample to measure the concentration of an analyte in the blood.

At least one of the above and other objects of the present invention may be realized by providing an apparatus for facilitating measurement of analyte concentration including a housing, an optical window in the housing, the housing having a through portion downstream of the optical window in a path of optical radiation supplied to the window, an optical output portion, downstream of the through portion in the path of optical radiation, which outputs optical radiation transmitted through a sample in the through portion to an analysis unit, and a transcutaneous access device securing the housing to a subject.

The optical output portion may include a reflective surface directing the optical radiation back through the through portion and the optical window. The reflective surface may be shaped to focus the optical radiation back through the through portion and the optical window. The reflective surface may include an active optical coating. The reflective surface may include a biologically active mirror coating which promotes vascular ingrowth.

The optical window may focus the optical radiation onto the through portion. The through portion may include a porous wall structure which promotes vascular ingrowth. The through portion may include a porous wall structure which prevents vascular ingrowth, while allowing interstitial fluid to pass therethrough. The size of the through portion may be fixed. The housing may be recessed within the transcutaneous access device The output optical portion may include another housing, another optical window in the another housing, the another optical window transmitting optical radiation generated by the sample in the through portion and another transcutaneous access portion in which the another housing is secured to the subject. The another optical window may be shaped to focus light passing therethrough.

At least one of the above and other objects of the present invention may be realized by providing system for measuring analyte concentration including a housing, an optical window in the housing, the housing having a through portion downstream of the optical window in the path of optical radiation supplied to the window, an optical output portion, downstream of the through portion in the path of optical radiation, which outputs optical radiation transmitted through a sample in the through portion, a transcutaneous access device holding the housing, an optical source for supplying optical radiation to the optical window, and a delivery system for supplying the optical radiation output by the optical output portion to instrumentation for analysis of analyte concentration.

The optical source may be one of an NIR source and a MIR source. The optical source may be fluorescence excitation within the housing. The optical source may be the body in which housing has been implanted.

At least one of the above and other objects of the present invention may be realized by providing a method of obtaining optical data for use in determining analyte concentration including implanting a transcutaneous access device in a subject, securing a sensor portion in the transcutaneous access device, the sensor portion including an optical window and a through portion downstream of the optical window in a path of optical radiation supplied to the optical window, providing optical radiation through the optical window to the through portion, and supplying optical radiation transmitted through a sample in the through portion, in response to the providing of the optical radiation, to instrumentation for determining a corresponding analyte concentration.

The supplying may include reflecting optical radiation transmitted by the sample in the through portion back through the through portion and the optical window. The supplying may include transmitting optical radiation transmitted by the sample in the through portion.

These and other objects of the present invention will become more readily apparent from the detailed description given hereinafter. However, it should be understood that the detailed description and specific examples, while indicating the preferred embodiments of the invention, are given by way of illustration only, since various changes and modifications within the spirit and scope of the invention will become apparent to those skilled in the art from this detailed description.

BRIEF DESCRIPTION OF THE DRAWINGS

The foregoing and other objects, aspects and advantages will be described with reference to the drawings, in which:

FIG. 1A is an elevational, perspective side view of the skin port sensor in accordance with the present invention;

FIG. 1B is an elevational cross-section of the skin port sensor shown in FIG. 1A;

FIG. 1C is an elevational, perspective side view of the transcutaneous access component according to one embodiment of the present invention;

FIG. 1D is an elevational, perspective side view of the sensor component according to one embodiment of the present invention;

FIG. 2A is an elevational side view of another embodiment of a transmission port in accordance with the present invention;

FIG. 2B is an elevational cross-section of the sensor component according to an embodiment of the present invention with a shaped reflective surface;

FIG. 2C is an elevational cross-section of the sensor component according to an embodiment of the present invention with a focusing optical window;

FIG. 2D is an elevational, perspective side view of the sensor component according to an embodiment of the present invention with an active optical coating;

FIG. 2E is an elevational, perspective side view of the sensor component according to an embodiment of the present invention with a porous housing element;

FIG. 2F is an elevational, perspective side view of the sensor component according to an embodiment of the present invention with a biologically active mirror coating;

FIG. 2G is an elevational cross-section of the sensor component according to an embodiment of the present invention with a recessed sensor;

FIG. 2H is an elevational cross-section of the sensor component according to an embodiment of the present invention with a prism;

FIG. 2I is an elevational cross-section of the sensor component according to an embodiment of the present invention with a set of mirrors;

FIG. 3A illustrates a side view of the skin port sensor of the present invention which has been implanted; and FIG. 3B illustrates a side view of the skin port sensor of the present invention which has been implanted and is in use with a fiber optic probe.

DETAILED DESCRIPTION

An embodiment of the present invention is illustrated in FIGS. 1A–1D. As shown in FIG. 1A, a skin port sensor 1 includes a transcutaneous access component 5 and a sensor component 10 having an optical window 35 and a reflective surface 40.

As shown in FIG. 1C, the access component 5 provides an infection-free and stable interface between the implant and the epidermis. The access component 5 consists of a flat, disc shaped skirt 15 having a central opening 16 and an array of through holes 17 distributed around the disk shaped skirt 15. Extending out from one side of the skirt in registration with the opening is an integral, tubular neck 20 whose lumen 22 is in registration with the opening of the skirt 16. The access component 5, including the skirt 15 and neck 20, is preferably formed of a flexible, thermally stable, biocompatible material such as flexible medical grade polyurethane. Preferably, the entire surface of the body of the skirt 15 and neck 20 is covered by a porous covering or bed 25 of a material such as polyester velour (U.S. Catheter and Instrumentation Company of Glenfalls, N.Y. Part N. 600k61121). The covering encourages cell infiltration and the formation of subcutaneous tissue and collagen. The overall design of the access component 5 may be as set forth in U.S. Pat. No. 5,662,616, which is hereby incorporated by reference in its entirety for all purposes.

In the present invention, the skirt 15 preferably has a diameter ranging from 0.5 to 4.0 cm, even more preferably about 2.5 cm. The thickness of the skirt 15 preferably may range from 0.1 to about 0.5 cm, even more preferably about 0.2 cm. The central opening 16 of the skirt and the lumen 22 of the neck preferably may range from 0.1 to 2.0 cm in diameter, even more preferably about 0.7 cm. The outer diameter of the neck 20 preferably may range from 0.25 to 2.0 cm, even more preferably about 1.0 cm. The height of the entire access component 5 preferably ranges from about 0.5 to about 2.5 cm, even more preferably about 1.0 cm.

As shown in FIG. 1D, the sensor component 10 of the skin port sensor provides a structure to facilitate efficient delivery of light to and from the tissue of interest. In the preferred embodiment, the sensor component 10 contains three main elements, a housing 30, the optical window 35, and the reflective surface 40. The housing 30 is preferably formed from a stainless steel tube or other rigid biocompatible material.

In the preferred embodiment, as shown in FIG. 1B, a proximal end 42 of the housing 30 is threaded or otherwise constructed to accept a fiber optic probe, e.g. an SMA 905 terminated fiber probe. The fiber optic probe may be terminated in any number of custom-made connectors configured to mate with the proximal end 42. The distal end 43 of the housing 30 is machined such that the distal lumen 44 of the housing 30 is slightly larger than the proximal lumen 45 of the housing 30. A lip 47 on the inside lumen is formed at the junction between the proximal and distal ends of the housing 30. The optical window 35 may be composed of materials such as borosilicate, Pyrex, fused silica, various other glass, but preferably sapphire (Edmund Scientific Part No. 1743365), and may be bonded using a medical grade epoxy (Loctite Corporation Part No. 4981) to the lip 47 formed between the proximal and distal ends of the housing element 30. A through passage 50 is machined on the distal lumen 44 to provide an area for tissue ingrowth or passage of interstitial fluid.

The reflective surface 40 is preferably composed of a polished biocompatible material either uncoated or coated with gold, aluminum, silver, titanium, or other reflective material and is secured within the distal lumen 44 of the housing element 30 opposite the optical window 35. The reflective surface 40 may be further coated with silicon monoxide in order to protect the reflective surface 40. Once constructed, the entire sensor component 10 may be secured using a medical grade epoxy to the lumen of the transcutaneous access component 5. Preferably, light used in conjunction with the sensor component is broad-band light and the reflection is a broad-band reflection. Alternatively, the reflection may have a specific, wavelength-dependent reflectivity for calibration.

The outer diameter of the housing element 30 may range from 0.1 to 2.0 cm, and is preferably about 0.7 cm. The diameter of the proximal lumen 45 of the housing element is preferably between 0.05 to 1.5 cm, and more preferably is about 0.3 cm. The diameter of the distal lumen 44 of the housing element 30 is preferably between 0.05 to 1.5 cm, and is more preferably about 0.5 cm. The optical window 35 and reflective surface 40 preferably may range in diameter from about 0.05 to 1.5 cm, more preferably being about 0.5 cm. The thickness of the optical window 35 is preferably between about 0.1 to 5.0 mm, even more preferably is about 1.0 mm. The thickness of the reflective surface 40 preferably may be between about 0.1 to 1.0 cm, and even more preferably is about 1.0 mm. The space 50 left for tissue ingrowth or interstitial fluid passage between the optical window 35 and the reflective surface 40 is preferably between 0.025 to about 2.0 mm, and even more preferably is about 0.4 mm.

FIG. 2A illustrates an alternative transmission embodiment of the port in accordance with the present invention. This port is designed to transmit light directly through a tissue for collection on the opposite end. The implant includes two opposing transcutaneous access components 60 with a central sensor component 65. The central sensor component no longer has a reflective surface. The distal end of the sensor component 70 and the proximal end of the sensor component 75 are preferably both threaded or otherwise constructed to accept a fiber optic probe. Two optical windows 80 are secured within the sensor component 65 at a fixed distance apart such that a through passage 85 for tissue ingrowth or interstitial fluid passage is created between the windows 80.

FIG. 2B illustrates a further embodiment of the skin port described above modified such that the reflective surface 40 is shaped to maximally direct light back out of the port for collection purposes.

FIG. 2C illustrates a further embodiment of the focusing optical window 35 in which the window is shaped like a lens to maximally direct light into the sample of interest. When used with the transmissive embodiment, one or both optical windows therein may be used to focus the optical radiation onto a desired target.

FIG. 2D illustrates another embodiment of the reflective surface 40 in which a spectrally active optical coating 90 is used thereon for reference and calibration purposes by determining tissue properties and path length, i.e., the length of the path traversed by the optical radiation. Calibration and reference can be determined by making spectroscopic measurements at the port site. For example, if an NIR transparent coating which appears blue is deposited onto the reflector surface, then measurement at two different wavelengths, e.g., wavelengths corresponding to blue and red light, would provide reference information which could be used for characterizing fiber losses, coupling efficiencies, or even scattering or absorptive changes in the tissue window itself since the relative intensity differences due to the coating 90 alone should be known a priori. Alternatively, the reference and calibration may be achieved using the visible reflection spectrum of gold reflector material itself. While the reflectivity of gold is relatively constant in the NIR spectrum, there is a notable reflectivity loss in the visible region below 500 nm or so. This inherent visible reflectivity difference can be used to provide reference or calibration information for the skinport sensor.

FIG. 2E illustrates another embodiment of the housing element 30 of the sensor component 10 in which the housing element 30 includes a porous wall structure 95 consisting of a material to promote vascular ingrowth. Alternatively, the porous wall structure 95 could be comprised of a material to prevent ingrowth, but still allow passage of interstitial fluid, thereby acting as a filter or membrane.

An example of such a material is a polymer membrane constructed using a hydrogel of photopolymerized poly (ethylene glycol) (PEG) as set forth in Pathak, C. P. et al. "Rapid Photopolymerization of Immunoprotective Gels in Contact with Cells and Tissue," *Journal of the American Chemistry Society*, Vol. 114, 1993, pp. 8311–8312, which is hereby incorporated by reference in its entirety. The PEG hydrogel prevents protein and cell deposition on the porous wall structure. Additionally, the PEG hydrogel facilitates mass-transfer of analytes within the interstitial fluid by limiting the formation of a fibrous capsule around the porous wall structure. In this embodiment, a specific chemical, which is able to change its optical properties by selectively binding the analyte of interest, could be included in the through passage of the sensor.

FIG. 2F illustrates an embodiment in which a biologically active mirror coating, such as a protein or enzyme known to promote vascular growth, is incorporated into a polymer coating 98 placed across the reflective surface 40. One such known promoter of angiogenesis is vascular endothelial growth factor (VEGF).

FIG. 2G illustrates an embodiment in which the central portion of the sensor component 10, i.e., primarily the housing 30, is recessed within the transcutaneous access component 5. This embodiment would improve the mechanical stability of the device by reducing the potential for interaction with external objects, as well as increase the aesthetic qualities of the device by making it less noticeable.

FIG. 2H illustrates an alternative transmission embodiment of the port in which a pair of prisms 92 are provided. A first prism directs light which enters the sensor component 10 in a vertical fashion through the through passage 50 containing the sample. A second prism then directs the light output from the through passage 50 back into the vertical direction out of the sensor component. The passage of the radiation through the sensor component 10 is illustrated by the arrows.

FIG. 2I illustrates an alternative transmission embodiment of the port in which the pair of prisms 92 in FIG. 2H are replaced with a pair of mirrors 93 to provide the same directing of the radiation through the sensor component 10 as indicated by the arrows. A transmissive element 94 is provided between the mirrors 93 to serve as the through passage for the sample.

Turning to the operation of the preferred embodiment of the present invention, referring to FIG. 3A, the skin port sensor 1 is implanted so that the skirt 15 of the access component 5 is anchored in the subcutaneous tissue 100 and the neck 20 of the access component 5 penetrates the dermal layer 105 and epidermal layer 110 of the skin. In time, fibrous collagen deposits in the holes 17 in the skirt 15 to help anchor the access component 5. These same holes 17 also allow for fluid drainage. The velour covering 25 provides a porous bed to encourage the growth of tissue and collagen around the skirt 15 to provide a biological seal with the epidermal cells which migrate or invaginate along the neck 20 until they reach the covering.

The sensor component 10, which is fixed within the access component 5, provides an optically transmissive window 35 through which light can be sent into the body without being affected by normal skin optics, skin temperature, or skin contaminants. The through passage 50 in the distal lumen 44 of the housing element 30 provides a pathway for tissue ingrowth or interstitial fluid flow between the optical window 35 and the reflective surface 40. This tissue ingrowth or interstitial fluid becomes the sample for any optical measurement made by the sensor.

In a preferred embodiment, as shown in FIG. 3B, the sensor is designed to be used in conjunction with a fiber optic probe 115. The implant functions by using the fiber optic probe 115 to send light into the skin port. A remote light source 120 could be a laser or light-emitting diode, but is preferably a broad band source with a filter to limit the light to a spectral region of interest. Light passes through the optical window 35 which provides a clear pathway to perform optical sensing on tissue, vasculature, or interstitial fluid located between the optical window 35 and reflective surface 40. The through passage 50 formed in the separation between the optical window 35 and the reflective surface 40 preferably is fixed to provide a fixed pathlength through which the light is able to interact with the tissue. The reflective surface 40 prevents the passage of light into tissue distal to the reflective surface 40 and results in light being reflected back out of the skin port. Light reflected out of the skin port is collected by the fiber optic probe 115 and returned to instrumentation designed to sense changes in characteristics of the light as a result of the interaction with analytes in the tissue.

Although a fiber optic probe 115 is used in the preferred embodiment, the skin port can be used with system which transmits light to and collects light from the device, including bulk optics, such as a collimating or focusing lens.

The skin port sensor of the present invention is preferably implanted in the abdomen for aesthetic reasons, but may be implanted anywhere on the body having a fatty soft tissue layer sufficiently thick to accommodate the protrusion of the skin port sensor into the subdermal space and where the risk of infection is not increased. Further, for durability, the skin port sensor is preferably placed somewhere on the body which is not subject to a lot of exposure or contact.

Once implanted, the skin sensor port can be calibrated for a particular user by comparing the measurement from the port with a well-established accurate method of measuring of the analyte being monitored, i.e., an invasive method. A set of calibration data may then be used to formulate a model for the sensor in order to accurately determine the analyte concentration from the measured data. The analyte concentration may be determined from the measured optical data in a known manner, such as those set forth in Coté, Gerard L. "Noninvasive Optical Glucose Sensing—An Overview" *Journal of Clinical Engineering*, July/August 1997, pp. 253–59, and in Vonach, R. et al. "Application of Mid-Infrared Transmission Spectrometry to the Direct Determination of Glucose in Whole Blood" *Applied Spectroscopy*, Vol. 52, No. 6, 1998, pp. 820–22, both of which are hereby incorporated by reference in their entirety. The model may be composed of several factors, which may be determined by performing prefiltering, wavelength selection, and/or partial least squares analysis, for example as set forth in Small, G. W., et al. "Strategies for Coupling Digital Filtering with Partial Least-Squares Regression: Application tot he Determination of Glucose in Plasma by Fourier Transform Near-Infrared Spectroscopy," *Analytical Chemistry*, Vol. 65, No. 1, 1993, pp. 3279–3289, Speigelman, Clifford H. et al. "Theoretical Justification of Wavelength Selection in PLS Calibration: Development of a New Algorithm" *Analytical Chemistry*, Vol. 70, No. 1, Jan. 1, 1998, pp. 35–44, and McShane, M. J., et al. "Assessment of Partial Least-Squares Calibration and Wavelength Selection for Complex Near-Infrared Spectra" *Applied Spectroscopy*, Vol. 52, No. 6, June 1998, pp. 878–884, which are hereby incorporated by reference in their entirety.

Further data may then be gathered, the analyte concentration may then be determined from these measurements in accordance with the model, and the resulting analyte concentrations may then be compared with the analyte concentrations determined using the established method. From these further measurements, the standard error of calibration and the standard error of prediction may be determined. Such a procedure is set forth, for example, in McShane, Michael et al. "Variable Selection in Multivariate Calibration of a Spectroscopic Glucose Sensor" *Applied Spectroscopy*, Vol. 51, No. 10, 1997, pp. 1559–64. The establishing of the model may be repeated until an acceptable level of the standard errors is achieved.

As seen from the foregoing, the skin port device provides a window to the body for performing optically based sensing. The device provides a means for removing changes in the optical signal due to variations in skin optics, pathlength, ambient temperature, and probe pressure. The device is based on a proven infection-free transcutaneous implant that forms a biological seal around the device. Therefore, the implant is suitable for long term use. Since the implant resides in the plane between the subcutaneous and dermal layers of tissue, subsequent removal is simple. Additionally, the skin port is a simple device that can be manufactured relatively easily and inexpensively. Once implanted, the optical analysis of the analyte concentration using the skin port sensor of the present invention is non-invasive.

While the above discussion has been directed to using near-infrared (NIR) absorption spectroscopy, it is to be understood that the skin port device of the present invention may be used to provide a window to the body for performing any other optically based sensing techniques and/or other optical regions. Such different regions include, for example, mid-infrared (MIR) absorption spectroscopy. Such different optically based sensing techniques include, for example, fluorescence, polarization, or Raman scatter.

Although the description above contains many specific details, these should not be construed as limiting the scope of the invention but as merely providing illustrations of some of the presently preferred embodiments of this invention. For example the skin port can have other shapes, materials, sizes and configurations. Further, for example, other techniques may be employed to determine the analyte concentration using the skin port sensor of the present invention. For example, because the skin port sensor of the present invention reduces scattering, Raman spectroscopy, including surface-enhanced Raman spectroscopy, could be employed.

While the present invention is described herein with reference to illustrative embodiments for particular applications, it should be understood that the present invention is not limited thereto. Those having ordinary skill in the art and access to the teachings provided herein will recognize additional modifications, applications, and embodiments within the scope thereof and additional fields in which the invention would be of significant utility without undue experimentation. Thus, the scope of the invention should be determined by the appended claims and their legal equivalents, rather than by the examples given.

What is claimed is:

1. An apparatus for facilitating measurement of analyte concentration comprising:
   a housing;
   an optical window in the housing, the housing having a through portion downstream of the optical window in a path of optical radiation supplied to the window;
   an optical output portion, downstream of the through portion in the path of optical radiation, which outputs optical radiation transmitted by a sample in the through portion to an analysis unit; and
   a transcutaneous access device adapted for securing the housing to a subject, wherein the housing is at a predetermined location relative to the transcutaneous access device.

2. The apparatus of claim 1, wherein the optical output portion comprises a reflective surface directing the optical radiation back through the through portion and the optical window.

3. The apparatus of claim 2, wherein the reflective surface is shaped to focus the optical radiation back through the through portion and the optical window.

4. The apparatus of claim 2, wherein the reflective surface includes an active optical coating.

5. The apparatus of claim 2, wherein the reflective surface comprises a biologically active mirror coating which promotes vascular ingrowth.

6. The apparatus of claim 1, wherein the optical window focuses the optical radiation onto the through portion.

7. The apparatus of claim 1, wherein the through portion comprises a porous wall structure which promotes vascular ingrowth.

8. The apparatus of claim 1, wherein the through portion comprises a porous wall structure which prevents vascular ingrowth, while allowing interstitial fluid to pass therethrough.

9. The apparatus of claim 1, wherein a size of the through portion is fixed.

10. The apparatus of claim 1, wherein the housing is recessed within the transcutaneous access device.

11. The apparatus of claim 1, wherein the output optical portion comprises another housing, another optical window in the another housing, the another optical window transmitting optical radiation transmitted by the sample in the through portion and another transcutaneous access portion in which the another housing is secured to the subject.

12. The apparatus of claim 11, wherein the another optical window is shaped to focus light passing therethrough.

13. A system for measuring analyte concentration comprising:
   a housing; an optical window in the housing, the housing having a through portion downstream of the optical window in the path of optical radiation supplied to the window
   an optical output portion, downstream of the through portion in the path of optical radiation, which outputs optical radiation transmitted by a sample in the through portion;
   a transcutaneous access device, adapted to be anchored to subcutaneous tissue of a patient, holding the housing at a predetermined location relative to the transcutaneous access device;
   an optical source for supplying optical radiation to the optical window; and a delivery system for supplying the optical radiation output by the optical output portion to instrumentation for analysis of analyte concentration.

14. The system of claim 13, wherein the optical source is one of an NIR source and a MIR source.

15. The system of claim 13, wherein said optical source is fluorescence excitation within the housing.

16. The system of claim 13, wherein said optical source is a body in which housing has been implanted.

17. The apparatus of claim 13, wherein the housing is recessed within the transcutaneous access device.

18. A method of obtaining optical data for use in determining analyte concentration comprising:

implanting a transcutaneous access device in a subject;

securing a sensor portion in the transcutaneous access device, the sensor portion including an optical window and a through portion downstream of the optical window in a path of optical radiation supplied to the optical window, wherein the through portion has a fixed distance relative to the transcutaneous access device;

providing optical radiation through the optical window to the through portion; and supplying optical radiation transmitted by a sample in the through portion in response to said providing to instrumentation for determining a corresponding analyte concentration.

19. The method of claim 18, wherein said supplying comprises reflecting optical radiation transmitted by the sample in the through portion back through the through portion and the optical window.

20. The method of claim 18, wherein said supplying comprises transmitting optical radiation transmitted by the sample in the through portion.

21. A method of obtaining optical data for use in determining analyte concentration comprising:

providing optical radiation from a source to a sensor portion of a device, wherein the sensor portion is affixed to a transcutaneous access portion of the device which is secured to a patient;

transmitting said optical radiation through the sensor portion, the sensor portion including an optical window and a through portion downstream of the optical window in a path of the optical radiation, wherein the optical window is at a fixed location with respect to the transcutaneous access portion; and supplying optical radiation that has been at least one of transmitted and reflected by a sample in the through portion to instrumentation for determining a corresponding analyte concentration.

22. The method of claim 21, wherein the step of supplying includes reflecting at least a portion of the optical radiation that has been transmitted by the sample toward the optical window.

23. The method of claim 21, wherein the step of supplying includes determining a corresponding analyte concentration based on optical radiation that has been transmitted by the sample.

24. An apparatus comprising:

a first portion adapted to be anchored in subcutaneous tissue of a patient;

a neck portion having a distal end, and a proximal end having an inside lumen, the neck portion extending from one side of the first portion, the proximal end adapted to be external the patient; and a sensor portion coupled to the neck portion to prevent subcutaneous access from the inside lumen of the proximal end.

25. The apparatus of claim 24, wherein the sensor portion further comprises an optical window.

26. The apparatus of claim 25, wherein the optical window is a fixed distance from the first portion.

* * * * *